US00PP15298P3

(12) United States Plant Patent
Black

(10) Patent No.: US PP15,298 P2
(45) Date of Patent: Nov. 9, 2004

(54) ***HYDRANGEA* PLANT NAMED 'BAILMER'**

(50) Latin Name: *Hydrangea macrophylla*
Varietal Denomination: Bailmer

(75) Inventor: Vernon Glen Black, Cottage Grove, MN (US)

(73) Assignee: Bailey Nurseries, Inc., St. Paul, MN (US)

( * ) Notice: Subject to any disclaimer, the term of this patent is extended or adjusted under 35 U.S.C. 154(b) by 0 days.

(21) Appl. No.: 09/972,369

(22) Filed: Oct. 9, 2001

(65) Prior Publication Data

US 2004/0123356 P1 Jun. 24, 2004

(51) Int. Cl.[7] ..... A01H 5/00

(52) U.S. Cl. ..... Plt./250

(58) Field of Search ..... Plt./250

*Primary Examiner*—Kent Bell

(74) *Attorney, Agent, or Firm*—Penny J. Aguirre

(57) ABSTRACT

A new cultivar of *Hydrangea macrophylla* named 'Bailmer' that is characterized by its ability to bloom on new growth without a cold requirement, its ability to dependably bloom in Zone 4, its deep green and comparatively mildew resistant foliage, and flowers that are either pink or blue in color depending on soil levels of available aluminum.

3 Drawing Sheets

Genus/species: *Hydrangea macrophylla.*
Varietal denomination: 'Bailmer'.

BACKGROUND OF THE INVENTION

The present invention relates to a new and distinct cultivar of *Hydrangea macrophylla* and will be referred to hereafter by its cultivar name, 'Bailmer'. 'Bailmer' represents a new Bigleaf *Hydrangea,* a deciduous shrub grown for landscape use and for use as a potted plant.

The inventor discovered the new cultivar, 'Bailmer', in a cultivated garden in St. Paul, Minn. in the summer of 1983. The inventor observed the new invention for a three year period and recognized that it was unique in that it bloomed dependably in a Zone 4 climate and consistently displayed deep green, disease-free foliage. The inventor rooted softwood cuttings and set up a trial block at a nursery in St. Paul, Minn. for further observation in 1986. In 1998, additional trials were initiated both in St. Paul, Minn. and in Athens, Ga. to fully identify the unique characteristics of 'Bailmer' as compared to existing cultivars of *H. macrophylla*.

It was discovered through ten years of trials, that the new cultivar had the ability to dependably initiate blooms on new growth and that plants grown from softwood cuttings initiate and develop blooms without a chilling requirement. The new cultivar can be kept in perpetual bloom until fall by the removal of old flowerheads. These characteristics are atypical for *Hydrangea macrophylla. H. macrophylla* cultivars typically bloom on buds formed the prior season on old wood and develop only after a period of chilling and the flower buds are often killed by the harsh winter conditions in Zone 4. The parental background of 'Bailmer' is unknown.

The extensive trials indicate that the combined characteristics identify 'Bailmer' as unique and unlike any other known cultivars of *H. macrophylla* known to the inventor and the experts consulted. In comparison, the cultivars 'Nikko Blue' (unpatented) and 'Général Vicomtesse de Vibraya' (unpatented) have flowers that are similar in color to 'Bailmer' and have better cold hardier than most, however, they do not bloom dependably on new wood.

Asexual reproduction of the new cultivar was first accomplished by softwood cuttings in St. Paul, Minn. in July of 1986 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Bailmer' from other varieties in commerce known to the inventor.

1. Blooms on new growth. Removal of spent blooms results in perpetual bloom from summer through fall.
2. Hardy in Zone 4.
3. Increased mildew resistance as compared to some cultivars; more resistance than 'Nikko Blue'.
4. Inflorescence color is pink, in alkaline soils and in any soils where aluminum levels or uptake is limited and blue in acidic with sufficient aluminum. The intensity and hue of the blue color is highly variable depending on soil pH and aluminum levels.
5. The ability to set flower buds on new growth without a cold treatment.
6. Foliage is deep green.

BRIEF DESCRIPTION OF THE DRAWING

The photograph in FIG. 1 is of a two year old plant of 'Bailmer' as grown outdoors in a three-gallon container in Athens, Ga. in June.

Figure 1:
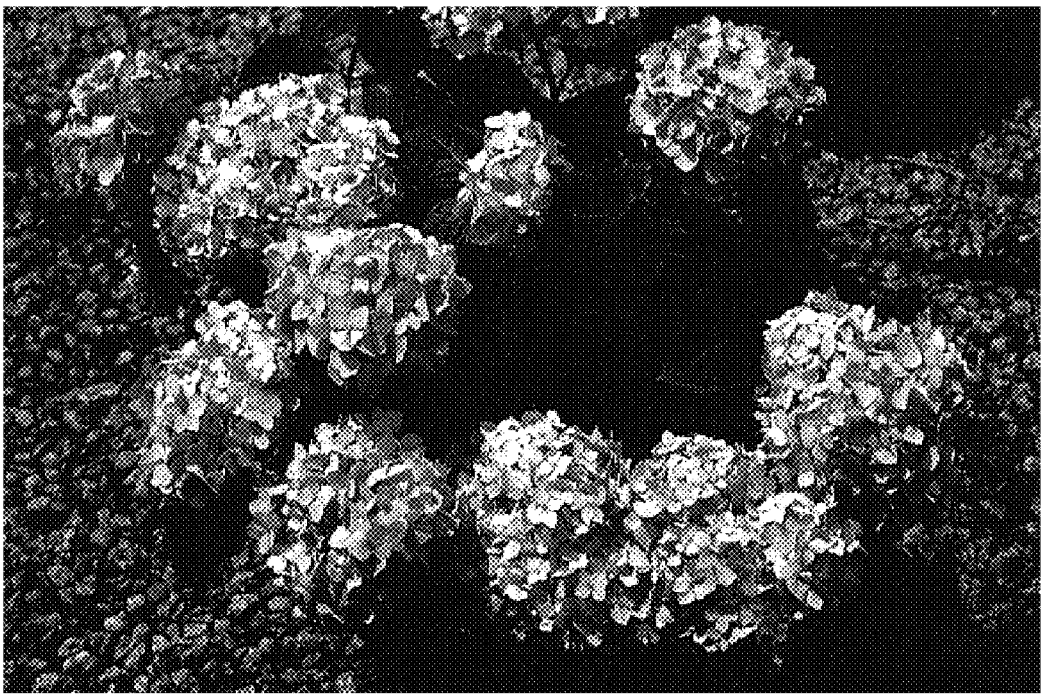
Figure 2:
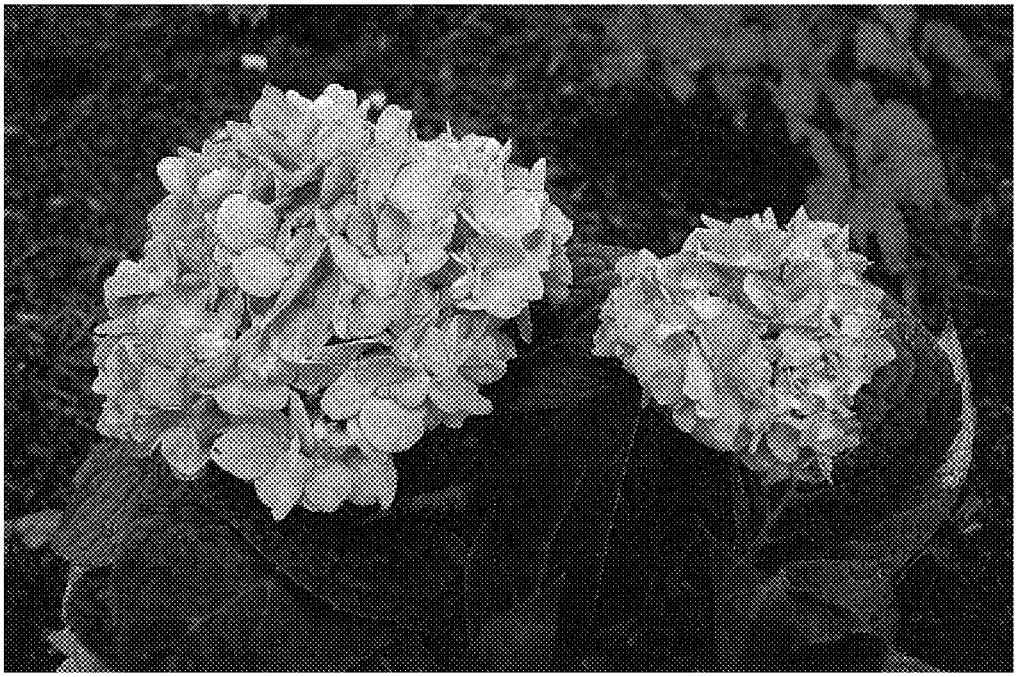
FIG. 2 shows a close up of both a fully open inflorescence on the left and a developing inflorescence on the right and was taken of a plant grown in a two-gallon container grown under outdoor conditions in St. Paul, Minn.
Figure 3:
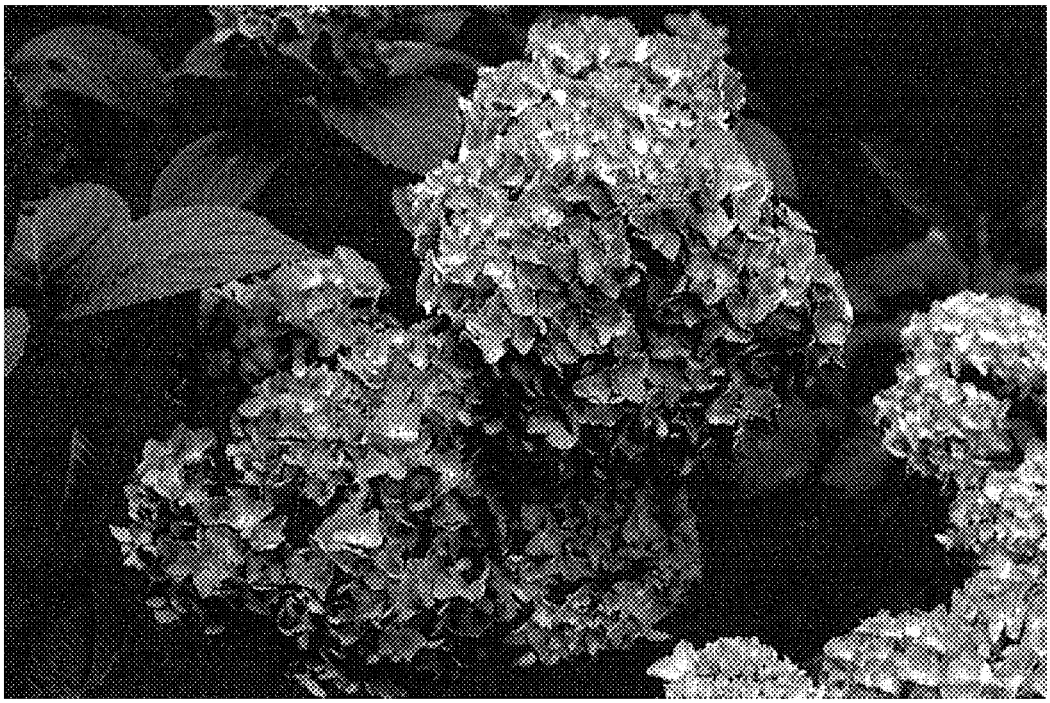

The photograph in FIG. 3 illustrates a plant in bloom that was grown outdoors in a three-gallon container in Athens, Ga. and treated with aluminum sulfate when buds become visible. The colors in the photographs are as close as possible with conventional photography.

BOTANICAL DESCRIPTION OF THE PLANT

The following is a detailed description of a one year old plant of the new cultivar as grown in a two gallon container under ambient light, outdoors in St. Paul, Minn. without treatment with aluminum sulfate: Phenotypic differences may be observed with variations in environmental, climatic, and cultural conditions. The color determination is in accordance with The 1995 R.H.S. Colour Chart of The Royal Horticultural Society, London, England, except where general color terms of ordinary dictionary significance are used.

Botanical classification: 'Bailmer' is a cultivar of *Hydrangea macrophylla.*

Commercial classification: Bigleaf *hydrangea.* Hortensia type.

Parentage: *Hydrangea macrophylla*, the exact seed and pollen parent are unknown.

General description:

*Blooming period.*—From June until frost in Minnesota and from June to November or frost in Georgia, if old flowerheads are removed.

*Plant habit.*—Compact, rounded, deciduous shrub.

*Height and spread.*—1.0 to 1.5 m in height and width.

*Hardiness.*—Zone 4–9.

*Culture.*—Grows best in moist but well-drained, humus-rich soil in full sun or partial shade with protection from high winds. Salt tolerant.

*Diseases and pests.*—Reasonably mildew resistant, more mildew resistant than 'Nikko Blue'. No susceptibility or resistance to other diseases or pests known to effect *H. macrophylla* has been observed.

*Root description.*—Fibrous.

Growth and propagation:

*Propagation.*—Softwood stem cuttings.

*Root initiation.*—7 to 10 days when grown at 65–70° F. in a greenhouse without supplemental lighting in Minnesota.

*Time required for root development.*—5 weeks to fully develop in a 32 cell in a media comprised of 50% perlite and 50% coconut fibers when grown at 65–70° F. in a greenhouse without supplemental lighting in Minnesota.

*Time required to produce a salable crop.*—A gallon container potted with a 32 cell plug is well-rooted and salable in 3 to 5 months depending on growing conditions.

Stem description:

*Shape shape.*—Round, solid.

*Stem color.*—New wood; 144B, speckled with 166B. Old wood (dormant); 199B.

*Stem diameter.*—Up to 5 mm on average.

*Stem surface.*—Glabrous.

*Internode length.*—3.5 to 7.0 cm in length.

*Branching.*—A single dormant stem will produce an average of 5 primary branches. Subsequent branching is determined by pinching; 2 stems develop per pinched node.

Foliage description:

*Leaf shape.*—Broadly elliptic.

*Leaf division.*—Simple.

*Leaf base.*—Varies from oblique to cuneate.

*Leaf apex.*—Acute or acuminate.

*Leaf venation.*—Penninerved, recessed, color 149D on upper and lower surface.

*Leaf margins.*—Serrated.

*Leaf attachment.*—Petiolate.

*Leaf arrangement.*—Opposite.

*Leaf surface.*—Upper; glabrous. Lower; glaucescent.

*Leaf color.*—Immature: Upper; 137C. Lower; 138B. Mature: Upper; Ranges from 137A to 139A as the leaf matures. Lower; 138A. Autumn color: Green or yellow depending on environmental conditions; not a distinguishing characteristic.

*Petiole size.*—1.0 to 3.0 cm in length, 3.0 to 5.0 mm in width.

*Petiole shape.*—Sulcate, no stipules.

*Petiole color.*—149D in color.

Flower description (sterile flowers):

*Type.*—Compound corymb, terminal and arising from new growth after pruning. Globose form. Most flowers are sterile (incomplete with only petaloids sepals and a center "eye" of unopened petals). Only 5 to 10% of the flowers are fertile (complete, small, insignificant and hidden under the sterile flowers). Descriptions of flower parts are for the sterile flowers with the exception of the reproductive organs.

*Lastingness of inflorescence.*—Persistent but color is retained for 2 to 4 weeks.

*Inflorescence size.*—7.5 to 15 cm in diameter.

*Inflorescence number.*—One per stem, number per plant is dependent on pruning. If flowers are removed when mature, approximately 26 blooms in a season.

*Flower number.*—Numerous, approximately 100 per inflorescence.

*Fragrance.*—None.

*Time required to develop an inflorescence from pruning.*—Approximately 8 weeks after developing 6 to 8 nodes of growth.

*Flower bud size.*—Up to 6 mm in length and 4 mm in width prior to opening.

*Flower bud color.*—145 B changing to 145C prior to opening.

*Peduncle size.*—3.5 to 5.0 cm in length and 3.5 to 6 mm in width.

*Peduncle color.*—144D speckled with 166B.

*Bract number.*—4–5 pairs.

*Bract color.*—144B maturing to 137A.

*Bract size.*—1 to 7 cm in length and 0.5 to 1.0 mm in width at peak bloom.

*Pedicel size.*—8 to 12 mm in length and 1 mm in width.

*Pedicel color.*—145C, changing to 62B, then 62C at peak bloom.

*Flower size.*—2.0 to 2.5 cm in diameter.

*Sepal shape.*—Orbicular, Aposepalous, partially overlapping.

*Sepal apex.*—Rounded.

*Sepal base.*—Acute.

*Sepal margin.*—Entire.

*Sepal number.*—4.

*Sepal size.*—10 to 15 mm in length and 8 to 12 mm in width.

*Sepal color* (*without aluminum treatment*).—Upper and lower surface; 145C when opening, changes to 157D in inner region and 62B on outer region, then the entire sepal changes to 62C at peak bloom. Fading of sepals as they dry is highly variable and dependent on soil moisture, those observed under the above conditions were 58A or 144D or a mosaic of those two colors.

*Sepal color* (*with aluminum treatment*).—Blue coloration is variable and dependent on level of available aluminum in the soil and availability (pH dependent). Color with sufficient aluminum uptake is 100C.

*Center* (*eye*) *size.*—2 mm in diameter.

*Center* (*eye*) *color.*—145C when flower is opening, changing to 145C, then to 62B, and finally to 62C at maturity.

Flower description (fertile flowers):

*Calyx.*—5 sepals, 2 mm in length, 1 mm in width, attached to a receptable 2 mm in length and width, 62C in color at maturity.

*Petals.*—5, 2 mm in length and width, 5 apopetalous, 62 C in color at maturity.

*Buds.*—2 mm in diameter and 62B in color prior to opening.

Reproductive organs (fertile flowers):

*Stamens.*—8–9, 2 to 4 mm in length and 0.3 mm in width, 63C in color, pollen is moderately abundant, pollen color is 201A at maturity, pollen is viable.

*Pistil.*—3, connate at the base, color 63C.

*Ovary.*—2 mm in diameter, inferior in flower and half inferior in fruit, 63C in color.

*Fruit.*—Capsule, held erect, 6 mm in length and 2 mm in width, yellow-brown in color with 3 apical, diverging woody styles, 2 to 3 mm in length and 1 mm in width. Seeds are numerous, viable and 200D in color.

It is claimed:

1. A new and distinct cultivar of *Hydrangea* plant named 'Bailmer' substantially as herein illustrated and described.

* * * * *